US007063852B2

(12) United States Patent
Clements (10) Patent No.: US 7,063,852 B2
(45) Date of Patent: Jun. 20, 2006

(54) HYBRID LT-A/CT-B HOLOTOXIN FOR USE AS AN ADJUVANT

(75) Inventor: John D. Clements, New Orleans, LA (US)

(73) Assignee: The Administrators of the Tulane Educational Fund, New Orleans, LA (US)

( * ) Notice: Subject to any disclaimer, the term of this patent is extended or adjusted under 35 U.S.C. 154(b) by 333 days.

(21) Appl. No.: 10/276,844

(22) PCT Filed: May 21, 2001

(86) PCT No.: PCT/US01/16542

§ 371 (c)(1),
(2), (4) Date: Nov. 19, 2002

(87) PCT Pub. No.: WO01/89456

PCT Pub. Date: Nov. 29, 2001

(65) Prior Publication Data

US 2003/0113345 A1 Jun. 19, 2003

Related U.S. Application Data

(60) Provisional application No. 60/205,969, filed on May 19, 2000.

(51) Int. Cl.
 *A61K 39/116* (2006.01)

(52) U.S. Cl. .................................. 424/203.1; 424/236.1; 424/235.1; 424/257.1; 424/261.1; 424/193.1; 424/197.11; 530/350

(58) Field of Classification Search ............... 424/236.1, 424/235.1, 257.1, 262.1, 193.1, 197.11, 203.1, 424/261.1; 530/350
See application file for complete search history.

(56) References Cited

U.S. PATENT DOCUMENTS

| 4,328,209 A | 5/1982 | Finkelstein et al. |
| 6,019,973 A | 2/2000 | Holmgren et al. |
| 6,149,919 A | 11/2000 | Domenighini et al. |

FOREIGN PATENT DOCUMENTS

| GB | 2217600 A | 11/1989 |
| WO | WO 92/19265 | 11/1992 |
| WO | WO 93/13202 | 7/1993 |
| WO | WO 95/17211 | 6/1995 |

OTHER PUBLICATIONS

Takeda et al. Infect. Immun. 1981. 34(2):341–6.*
Rodighiero et al. 1998. Biochem. Soc. Trans. 26(4):S364.*
Häse et al., 1994, "Construction and characterization of recombinant *Vibrio cholerae* strains producing inactive cholera toxin analogs", Infect. Immun. 62(8):3051–3057.

McGhee et al., 1994, "Vaccines for mucosal immunity: Unique delivery system and immune response analyses for Th1/TH2 cells and IgE/IgA B cells", Mucosal Immunology Update, Spring 1994, Raven Press, New York p. 21.

Moss et al., 1993, "Interaction of ADP–ribosylation factor with *Escherichia coli* enterotoxin that contains an inactivating lysine 112 substitution", J. Biol. Chem. 268(9):6383–6387.

Conner et al., 1993, "Rotavirus vaccine administered parenterally induces protective immunity", J. Virol. 67(11):6633–6641.

Santiago et al., 1993, "Oral immunization of rats with proteinoid microspheres encapsulating influenza virus antigens", Pharmaceutical Research 10(8):1243–1247.

Gould–Fogerite and Mannino, 1993, In: Liposome Technology, Second Edition, vol. III, Gregoriadis (ed.), CRC Press, Boca Raton pp. 261–276.

Clements et al., 1992, In: Recombinant DNA vaccines: Rationale and Strategy, Isaacson (ed.), Marcel Decker, New York pp. 293–321.

Cardenas and Clements, 1992, "Oral immunization using live attenuated *Salmonella* spp. as carriers of foreign antigens", Clin. Microbiol. Rev. 5(3):328–342.

Lycke et al., 1992, "The adjuvant effect of Vibrio cholerae and *Escherichia coli* heat–labile enterotoxins is linked to their ADP–ribosyltransferase activity", Eur. J. Immunol. 22:2277–2281.

Garcon and Six, 1991, "Universal vaccine carrier: Liposomes that provide T–dependent help to weak antigens", J. Immunol. 146:3697–3702.

Clements and Cardenas, 1990, "Vaccines against enterotoxigenic bacterial pathogens based on hybrid *Salmonella* that express heterologous antigens", Res. Microbiol. 141:981–993.

Brandtzaeg, 1989, "Overview of the mucosal immune system", Curr. Top. Microbiol. Immunol. 146:13–25.

Elson, 1989, "Cholera toxin and its subunits as potential oral adjuvants", Curr. Topics Microbiol. Immunol. 146:29–33.

(Continued)

*Primary Examiner*—Jennifer E. Graser
(74) *Attorney, Agent, or Firm*—Jones Day (57) ABSTRACT

The present invention provides a novel composition which is a hybrid heat labile enterotoxin comprising the A-subunit of the heat labile toxin of *Escherichia coli* (LT-A) and the B-subunit of the cholera enterotoxin of *Vibrio cholerae* (CT-B). The hybrid toxin is designated LT-A/CT-B. The LT-A subunit, the CT-B subunit, or both subunits of the hybrid toxin may be mutant subunits, e.g., differing from wild-type subunits by amino acid substitutions, deletions or additions. Also provided are methods of using the novel LT-A/CT-B comprising compositions of the invention as adjuvants for vaccines, methods of making the LT-A/CT-B hybrid holotoxin, and kits.

2 Claims, 6 Drawing Sheets

Liang et al., 1988, "Oral administration of cholera toxin–Sendai virus conjugate potentiates gut and respiratory immunity against Sendai virus", J. Immunol. 141(5):1495–1501.

Clemens et al., 1988, "Cross–protection by B subunit–whole cell cholera vaccine against diarrhea associated with heat–labile toxin–producing enterotoxigenic *Escherichia coli*: Results of a large–scale field trial", J. Infect. Dis. 158(2):372–377.

Clements et al., 1988, "Adjuvant activity of *Escherichia coli* heat–labile enterotoxin and effect on the induction of oral tolerance in mice to unrelated protein antigens", Vaccine 6:269–277.

Clements et al., 1988, "*Escherichia coli* heat–labile enterotoxin possesses adjuvant activity and prevents the induction of oral tolerance in mice to unrelated protein antigens", Abstract No. B–91, 88th Ann. Meet. Am. Soc. Microbiol.

Alving et al., 1986, "Effectiveness of liposomes as potential carriers of vaccines: Applications to cholera toxin and human malaria sporozoite antigen", Vaccine 4:166–172.

Owen et al., 1986, "M cell transport of *Vibrio cholerae* from the intestinal lumen into Peyer's patches: A mechanism for antigen sampling and for microbial transepithelial migration", J. Infect. Dis. 153(6):1108–1118.

Lycke and Holmgren, 1986, "Strong adjuvant properties of cholera toxin on gut mucosal immune responses to orally presented antigens", Immunology 59:301–308.

Cebra et al., 1986, In: Vaccines 86, Brown et al. (eds.), Cold Spring HArbor Laboratory, New York pp. 129–133.

Elson and Ealding, 1984, "Cholera toxin feeding did not induce oral tolerance in mice and abrogated oral tolerance to an unrelated protein antigen", J. Immunol. 133(6):2892–2897.

Clements and El–Morshidy, 1984, "Construction of a potential live oral bivalent vaccine for typhoid fever and cholera–*Escherichia coli*–related diarrheas", Infect. Immun. 46(2):564–569.

Strober and Jacobs, 1985, In: Advances in host defense mechanisms, vol. 4., Mucosal Immunity, Gallin and Fauci (eds.), Raven Press, New York, pp. 1–30.

Tomasi and Plaut, 1985, In: Advances in host defense mechanisms, vol. 4, Mucosal Immunity, Gallin and Fauci (eds.), Raven Press, New York, pp. 31–61.

McKenzie and Halsey, 1984, Cholera toxin B subunit as a carrier protein to stimulate mucosal immune response, J. Immunol. 133(4):1818–1824.

Elson and Ealding, 1984, "Generalized systemic and mucosal immunity in mice after mucosal stimulation with cholera toxin", J. Immunol. 132(6):2736–2741.

Svennerholm et al., 1984, "Mucosal antitoxic and antibacterial immunity after cholera disease and after immunization with a combined B subunit–whole cell vaccine", J. Infect. Dis. 149(6):884–893.

Pierce et al., 1983, "Procholeragenoid: A safe and effective antigen for oral immunization against experimental cholera", Infect. Immun. 40(3):1112–1118.

Clements et al., 1983, "Cloning and molecular characterization of the B subunit of *Escherichia coli* heat–labile enterotoxin", Infect. Immun. 40:653–658.

Dallas and Falkow, 1980, "Amino acid sequence homology between cholera toxin and *Escherichia coli* heat–labile toxin", Nature 288:499–501.

Clements et al., 1980, "Properties of homogenous heat–labile enterotoxin from *Escherichia coli*", Infect. Immun. 29:91–97.

Field, 1980, In: Secretory diarrhea, Field et al., (eds.) Waverly Press, Baltimore, pp. 21–30.

Clements and Finkelstein, 1979, "Isolation and characterization of homogenous heat–labile enterotoxins with high specific activity from *Escherichia coli* cultures", Infect. Immun. 24:760–769.

Clements and Finkelstein, 1979, "Demonstration of shared and unique immunological determinants in enterotoxins from Vibrio cholerae and *Escherichia coli*", Infect. Immun. 22:709–713.

Clements and Finkelstein, 1978, "Immunological cross–reactivity between a heat–labile enterotoxin(s) of *Escherichia coli* and subunits of Vibrio cholerae enterotoxin", Infect. Immun. 21:1036–1039.

Finkelstein, 1975, "Immunology of cholera", Curr. Top. Microbiol. Immunol. 69:139–196.

Bockman and Cooper, 1973, "Pinocytosis by epithelium associated with lymphoid follicles in the bursa of fabricius, appendix, choleragenoid", J. Exp. Med. 130:185–202.

Douce et al., 1995, "Mutants of *Escherichia coli* heat–labile toxin lacking ADP–ribosyltransferase activity act as nontoxic, mucosal adjuvants", Proc Natl Acad Sci 92:1644–1648.

Lobet et al., 1991, "Effect of site–directed mutagenic alterations on ADP–ribosyltransferase activity of the A subunit of *Escherichia coli* heat–labile enterotoxin", Infection and Immunity 59(9):2870–2879.

Burnette et al., 1991, "Site–specific mutagenesis of the catalytic subunit of cholera toxin: Substituting lysine for arginine 7 causes loss of activity", Infection and Immunity 59(11):4266–4270.

Okamoto et al., 1988, "Effect of substitution of glycine for arginine at position 146 of the A1 subunit on biological activity of *Escherichia coli* heat–labile enterotoxin", J Bacteriol 170(5):2208–2211.

Holmgren et al., 1993, *Vaccine* 11:1179–1184.

Holmgren et al., 1994, *Am J. Trop. Med Hyg* 50:42–54.

Loossmore et al., 1990 *Infec. Immun.*, 58(11):3653.

Walker et al., 1993, *Vaccine Res.* 2(1):1–10.

Rodighiero et al., Structural Basis for the Differential Toxicity of Cholera Toxin and *Escherichia coli* Heat–labile Enterotoxin, J. Biol. Chem., 1999, 264(7):3962–3969.

* cited by examiner

HYBRID LT-A/CT-B HOLOTOXIN FOR USE AS AN ADJUVANT

This application is a national stage of International Application No. PCT/US01/16542, filed May 21, 2001, which claims the benefit under 35 U.S.C. Section 119(e) of U.S. provisional application 60/205,969, filed May 19, 2000.

The U.S. Government has a paid-up license in this invention and the right in limited circumstances to require the patent owner to license others on reasonable terms as provided for by the terms of Public Health service grant AI42777 awarded by the National Institute of Allergy and Infectious Disease.

1. FIELD OF THE INVENTION

The present invention is directed towards a novel composition which is a hybrid heat labile enterotoxin holotoxin comprising the A-subunit of the heat labile toxin of *Escherichia coli* (LT-A) and the B-subunit of the cholera enterotoxin of *Vibrio cholerae* (CT-B). The hybrid toxin is designated LT-A/CT-B. The LT-A subunit, the CT-B subunit, or both subunits of the hybrid holotoxin may be mutant subunits, e.g., differing from wild-type subunits by one or more amino acid substitutions, deletions or additions.

2. BACKGROUND OF THE INVENTION

Each year, infectious diseases kill more than 17 million people, including 9 million children. In the United States, deaths due to infectious diseases increased 58 percent from 1982 to 1992 and are now third in the leading causes of death. In addition to suffering and death, infectious diseases impose an enormous financial burden on society. The majority of those infections and deaths are caused by organisms that first make contact with and then either colonize or cross mucosal surfaces to infect the host.

While vaccination is the most cost-effective means of controlling infectious disease morbidity and mortality, traditional vaccine strategies that involve parenteral immunization (via needle) with inactivated viruses or bacteria or subunits of relevant virulence determinants of those pathogens do not prevent those interactions. In fact, traditional vaccine strategies do not prevent infection but instead resolve infection before disease ensues. In some cases, HIV for example, once the virus crosses the mucosal surface and enters the host cell, be that a dendritic cell, an epithelial cell, or a T-cell, the host-parasite relationship is moved decidedly in favor of the parasite (HIV). In that case, as in many others, a vaccine strategy that does not prevent the initial infection of the host is unlikely to succeed.

Recently, a great deal of attention has focused on mucosal immunization as a means of inducing secretory IgA (S-IgA) antibodies directed against specific pathogens of mucosal surfaces. The rationale for this is the recognition that S-IgA constitutes greater than 80% of all antibodies produced in mucosal-associated lymphoid tissues in humans and that S-IgA may block attachment of bacteria and viruses, neutralize bacterial toxins, and even inactivate invading viruses inside of epithelial cells. In addition, the existence of a Common Mucosal Immune System permits immunization on one mucosal surface to induce secretion of antigen-specific S-IgA at distant mucosal sites. It is now appreciated that mucosal immunization may be an effective means of inducing not only S-IgA but also systemic antibody and cell-mediated immunity.

The mucosal immune response can be divided into two phases (McGhee and Kiyono 1993, Infect. Agents. Dis. 12:55–73). First, the inductive phase involves antigen presentation and the initiation events which dictate the subsequent immune response. During the initiation events, antigen-specific lymphocytes are primed and migrate from the inductive sites (e.g., Peyer's patches in the enteric mucosa) through the regional lymph nodes, into the circulation and back to mucosal effector sites (e.g. lamina propria). Once these effector cells have seeded their effector sites, the second phase, or effector phase, of the mucosal immune response can occur. A significant difference between mucosal immunization and parenteral immunization is that both mucosal and systemic immunity can be induced by mucosal immunization while parenteral immunization generally results only in systemic responses.

Most studies on the mucosal immune response conducted to date have dealt with the secretory antibody component of the mucosal response and the complex regulatory issues involved with induction of S-IgA following mucosal immunization and not with the systemic antibody response or cellular immunity induced by mucosal immunization. In that regard, it is important to understand the type of helper T lymphocyte response induced by mucosal immunization since the type of helper T lymphocyte stimulated by an antigen is one of the most important factors for defining which type of immune response will follow. At least two different types of helper T lymphocytes (Th) which can be distinguished based on cytokine secretion have been identified in mice (Cherwinski et al. 1987, Journal of Experimental Medicine 166:1229–1244; Mosmann and Coffman 1989, Annual Reviews of Immunology 7:145–173), humans (Romagnani 1991, Immunology Today 12:256–257) and other animal species (Brown et al. 1994, Infection and Immunity 62:4697–4708). Th1 lymphocytes secrete substantial amounts of IL-2 and IFN-gamma and execute cell-mediated immune responses (e.g. delayed type hypersensitivity and macrophage activation), whereas Th2 lymphocytes secrete IL-4, IL-5, IL-6 and IL-10 and assist in antibody production for humoral immunity. Theoretically then, antigenic stimulation of one T helper cell subset and not the other would result in production of a particular set of cytokines which would define the resulting immune response.

The presence of these cytokines coupled with an antigenic stimulus presented by macrophages in the context of Class II MHC molecules can initiate a Th1 type responses. The ability of Th1 cells to secrete IL-2 and IFN-gamma further amplifies the response by activating Th1 cells in an autocrine fashion and macrophages in a paracrine fashion. These activated leukocytes can release additional cytokines (e.g., IL-6) which may induce the proliferation and differentiation of antigen specific B lymphocytes to secrete antibody (the effector phase). In this scenario, the predominant isotype secreted by murine B lymphocytes is often IgG2a. In a second scenario (Urban et al. 1992, Immunol. Rev. 127:205–220), antigens such as allergens or parasites can effectively stimulate a Th2 lymphocyte response (the inductive phase). Presentation of such antigens to Th2 cells can result in the production of the lymphokines IL-4 and IL-5 which can induce antigen specific B lymphocytes to secrete IgE and IgG1 or induce eosinophilia, respectively (the effector phase). Furthermore, stimulated Th2 cells can secrete IL-10 which has the ability to specifically inhibit secretion of IL-2 and IFN-gamma by Th1 lymphocytes and also to inhibit macrophage function.

It is obvious that the type of T helper cell stimulated affects the resultant cellular immune response as well as the predominant immunoglobulin isotype secreted. Specifically, IL-4 stimulates switching to the IgE and IgG1 isotypes whereas IFN-gamma stimulates IgG2a secretion. Numerous studies, predominantly conducted in vitro, have suggested that IL-5, IL-6 and TGF-beta can cause isotype witching to IgA.

2.1. Bacterial Enterotoxins as Mucosal Adjuvants

Despite the attractiveness of mucosal vaccination for inducing both mucosal and systemic immune responses, mucosally administered antigens are frequently not immunogenic. A number of strategies have been developed to facilitate and enhance the immune response obtained after mucosal immunization. Among these strategies are the use of attenuated mutants of bacteria (i.e., *Salmonella* spp.) as carriers of heterologous antigens, encapsulation of antigens into microspheres, gelatin capsules, different formulations of liposomes, adsorption onto nanoparticles, use of lipophilic immune stimulating complexes, and addition of bacterial products with known adjuvant properties. While a number of substances of bacterial origin have been tested as mucosal adjuvants (Lowell et al. 1997, Journal of Infectious Diseases 175:292–301; Roberts et al. 1995, Infection and Immunity 63:2100–2108; Van De Verg et al. 1996, Infection and Immunity 64:5263–5268), the two bacterial proteins with the greatest potential to function as mucosal adjuvants are cholera toxin (CT), produced by various strains of *Vibrio cholerae*, and the heat-labile enterotoxin (LT) produced by some enterotoxigenic strains of *Escherichia coli* (Clements et al. 1988, Vaccine 6:269–277; Elson 1989, Immunology Today 146:29–33; Lycke et al. 1992, European Journal of Immunology 22:2277–2281; Xu-Amano et al. 1993, Journal of Experimental Medicine 178:1309–1320).

Although LT and CT have many features in common, these are clearly distinct molecules with biochemical and immunologic differences which make them unique (see below). Both LT and CT are synthesized as multisubunit toxins with A and B components. On thiol reduction, the A component dissociates into two smaller polypeptide chains. One of these, the A1 piece, catalyzes the ADP-ribosylation of the stimulatory GTP-binding protein (GSa) in the adenylate cyclase enzyme complex on the basolateral surface of the epithelial cell resulting in increasing intracellular levels of cAMP. The resulting increase in cAMP causes secretion of water and electrolytes into the small intestine through interaction with two cAMP-sensitive ion transport mechanisms involving 1) NaCl cotransport across the brush border of villous epithelial cells, and 2) electrogenic Na dependent Cl secretion by crypt cells (Field, 1980, In: Field M, Fordtran J S, Schultz S G, editors. Secretory diarrhea. Baltimore, Md.: Waverly Press. p 21–30). The B-subunit binds to the host cell membrane receptor (ganglioside GM1) and facilitates the translocation of the A-subunit through the cell membrane.

Recent studies have examined the potential of CT and LT to function as mucosal adjuvants against a variety of bacterial and viral pathogens using whole killed organisms or purified subunits of relevant virulence determinants from these organisms. Representative examples include tetanus toxoid (Xu-Amano et al. 1994, Vaccine 12:903–911; Xu-Amano et al. 1993, Journal of Experimental Medicine 178:1309–1320; Yamamoto et al. 1997a, Proceedings of the National Academy of Sciences 94:5267–5272; Yamamoto et al. 1997b, Journal of Experimental Medicine 185:1203–1210), inactivated influenza virus (Gluck et al. 1999, J Virol 73(9):7780–6; Hashigucci et al. 1996, Vaccine 14:113–119; Katz et al. 1996, In: Brown L E, Hampson A W, Webster R G, editors. Options for the control of influenza. III. New York: Elsevier Science. p 292–297; Katz et al. 1997, Journal of Infectious Diseases 175:352–363; Komase et al. 1998, Vaccine 16(2–3):248–254), recombinant urease from *Helicobacter* spp. (Lee et al. 1995, Journal of Infectious Diseases 172:161–171; Weltzin et al. 1997, Vaccine 4:370–376), pneumococcal surface protein A from *Streptococcus pneumoniae* (Wu et al. 1997, Journal of Infectious Diseases 175:839–846), Norwalk virus capsid protein (Mason et al. 1996, Proceedings of the National Academy of Sciences 93:5335–5340), synthetic peptides from measles virus (Hathaway et al. 1995, Vaccine 13:1495–1500), and the HIV-1 peptides (Staats et al. 1996, Journal of Immunology 157:462–472). There are many other examples and it is clear from these studies that both LT and CT have significant potential for use as adjuvants for mucosally (and otherwise) administered antigens. This raises the possibility of an effective immunization program against a variety of pathogens involving the administration of killed or attenuated organisms or relevant virulence determinants of specific agents in conjunction with LT or CT, preferably mucosally. However, the fact that these toxins stimulate a net lumenal secretory response may prevent their use for practical vaccine applications. For instance, it was observed that as little as 5 μg of purified CT administered orally was sufficient to induce significant diarrhea in human volunteers while ingestion of 25 μg of CT elicited a full 20-liter cholera purge (Levine et al. 1983, Microbiological Reviews 47:510–550).

In recently conducted volunteer studies with LT administered alone or in conjunction with the *V. cholerae* Whole Cell/B-Subunit Vaccine, LT was shown to induce fluid secretion at doses as low as 2.5 μg when administered in conjunction with the vaccine, while 25 μg of LT elicited up to 6-liters of fluid secretion. While the adjuvant effective dose in humans for either of these toxins has not been established, experiments in animals suggest that it may be comparable to the toxic dose. Taken together, these studies suggest that while LT and CT may be attractive as adjuvants, studies in animals do not reflect the full toxic potential of these molecules in humans, and that toxicity may seriously limit their practical use.

2.2. Differences Between CT and LT

As mentioned above, although LT and CT have many features in common, these are clearly distinct molecules with biochemical and immunologic differences which make them unique (Dickinson and Clements, 1996, In: Kiyono H, Ogra P L, McGhee J R, editors. Mucosal Vaccines. San Diego, Calif.: Academic Press. p 73–87). For example, LT has an unusual affinity for carbohydrate containing matrices (Clements and Finkelstein 1979, Infection and Immunity 24:760–769; Clements et al. 1980, Infection and Immunity 24:91–97). LT binds not only to agarose in columns used for purification but, more importantly, to other biological molecules containing galactose, including glycoproteins and lipopolysaccharides. This lectin-like binding property of LT results in a broader receptor population on mammalian cells for LT than for CT which binds only to GM1 (Angstrom et al. 1994, Proc Natl Acad Sci U S A 91(25):11859–63; Clements et al. 1980, Infection and Immunity 24:91–97; Holmgren, 1994, Progress in Brain Research 101:163–177). Moreover, LT and CT generally activate different subsets of T helper cells. CT promotes $CD4^+$ Th2-type responses and help for IgG1, IgE and mucosal IgA while LT induces both $CD4^+$ Th1- and Th2-type responses and help for IgG1, IgG2a, IgG2b, and mucosal IgA (Marinaro et al. 1995, Journal of Immunology 155:4621–4629; Xu-Amano et al. 1993, Journal of Experimental Medicine 178:1309–1320). This distinction between LT and CT may be important in terms of selecting a mucosal adjuvant for use with specific categories of pathogens, assuming the Th2 bias holds. Possible sources for this bias include the availability of different receptors for LT and CT, mentioned above, differences in intracellular localization based upon differences in ER-signal sequences between CT and LT, and differences in activation of intracellular signaling pathways. CT, LT strains obtained from human hosts, and LT strains obtained from porcine hosts have -KDEL, -RNEL, and -RDEL, respectively, as ER retention signals.

2.3. Development of Non-Toxic Mucosal Adjuvants

A number of attempts have been made to alter the toxicity of LT and CT, most of which have focused on eliminating enzymatic activity of the A-subunit associated with enterotoxicity. The majority of these efforts have involved the use of site-directed mutagenesis to change amino acids associated with the crevice where NAD binding and catalysis is thought to occur. Recently, a model for NAD binding and catalysis was proposed (Domenighini et al. 1994, Molecular Microbiology 14:41–50; Pizza et al. 1994, Molecular Microbiology 14:51–60) based on computer analysis of the crystallographic structure of LT (Sixma et al. 1993, Journal of Molecular Biology 230:890–918; Sixma et al. 1991, Nature (London) 351:371–377). Replacement of any amino acid in CT or LT involved in NAD-binding and catalysis by site-directed mutagenesis has been shown to alter ADP-ribosyltransferase activity with a corresponding loss of toxicity in a variety of biological assay systems (Burnette et al. 1991, Infection and Immunity 59:4266–4270; Fontana et al. 1995, Infection and Immunity 63:2356–2360; Harford et al. 1989, European Journal of Biochemistry 183:311–316; Hase et al. 1994, Infection and Immunity 62:3051–3057; Lobet et al. 1991, Infection and Immunity 59:2870–2879; Lycke et al. 1992, European Journal of Immunology 22:2277–2281; Merritt et al. 1995, Nature Structural Biology 2:269–272; Moss et al. 1993, Journal of Biological Chemistry 268:6383–6387; Pizza et al. 1994, Molecular Microbiology 14:51–60; Tsuji et al. 1991, FEBS Letters 291:319–321; Tsuji et al. 1990, Journal of Biological Chemistry 265:22520–22525; Yamamoto et al. 1997a, Proceedings of the National Academy of Sciences 94:5267–5272; Yamamoto et al. 1997b, Journal of Experimental Medicine 185:1203–1210). The adjuvanticity potential of some of these mutants has been tested on animal models using a variety of coadministered antigens (DiTommaso et al. 1996, Infection and Immunity 64:974–979; Lycke et al. 1992, European Journal of Immunology 22:2277–2281; Partidos et al. 1996, Immunology 89:483–487; Yamamoto et al. 1997a, Proceedings of the National Academy of Sciences 94:5267–5272; Yamamoto et al. 1997b, Journal of Experimental Medicine 185:1203–1210). In addition, it has been shown that exchanging K for E112 in LT not only removes ADP-ribosylating enzymatic activity, but cAMP activation and adjuvant activity as well (Lycke et al. 1992, European Journal of Immunology 22:2277–2281). A logical conclusion from the Lycke et al. studies is that ADP-ribosylation and induction of cAMP are essential for the adjuvant activity of these molecules. As a result, a causal linkage has been established between adjuvanticity and enterotoxicity. That is, the accumulation of cAMP responsible for net ion and fluid secretion into the gut lumen was thought to be a requisite to adjuvanticity (see below).

Dickinson and Clements (Dickinson and Clements, 1995, Infection and Immunity 63:1617–1623) explored an alternate approach to dissociation of enterotoxicity from adjuvanticity. Like other bacterial toxins that are members of the A-B toxin family, both CT and LT require proteolysis of a trypsin sensitive bond to become fully active. In these two enterotoxins, that trypsin sensitive peptide is subtended by a disulfide interchange that joins the A1 and A2 pieces of the A-subunit. In theory, if the A1 and A2 pieces cannot separate, A1 may not be able to find its target (adenylate cyclase) on the basolateral surface or may not assume the conformation necessary to bind or hydrolyze NAD.

Dickinson and Clements constructed a mutant of LT using site-directed mutagenesis to create a single amino acid substitution within the disulfide subtended region of the A subunit separating A1 from A2. This single amino acid change altered the proteolytically sensitive site within this region, rendering the mutant insensitive to trypsin activation. The physical characteristics of this mutant were examined by SDS-PAGE, its biological activity was examined on mouse Y-1 adrenal tumor cells and Caco-2 cells, its enzymatic properties determined in an in vitro NAD:agmatine ADP-ribosyltransferase assay, and its immunogenicity and immunomodulating capabilities determined by testing for the retention of immunogenicity and adjuvanticity. This mutant LT, designated LT(R192G), has been shown to be an effective mucosal adjuvant and has recently been evaluated in a series of Phase I safety studies. LT(R192G) is the subject of U.S. Pat. No. 6,019,982 (Mutant enterotoxin effective as a non-toxic oral adjuvant). Clements also constructed a double-mutant LT, LT(R192G/L211A), which has even further reduced toxicity (U.S. Pat. No. 6,033,673).

Tsuji et al. (Tsuji et al. 1997, Immunology 90:176–182) recently demonstrated that a protease-site deletion mutant LT($\Delta$192–194) also lacks in vitro ADP-ribosylagmatine activity, has a ten-fold reduction in enterotoxicity in rabbit ligated ileal loops, and a 50% reduction and delayed onset of cAMP induction in cultured myeloma cells. LT($\Delta$192–194) was shown to have increased adjuvant activity for induction of serum IgG and mucosal IgA against measles virus when compared to native LT, LT-B, or LT(E112K). LT($\Delta$192–194) was effective when administered intranasally, subcutaneously, intraperitoneally, or orally, although mucosal IgA responses were only demonstrated following mucosal administration. These investigators also demonstrated increased adjuvant activity for mucosally administered LT($\Delta$192–194) in conjunction with KLH, BCG, and Ova.

Other mutants have also been created and tested. The first of those is the active-site mutant of LT designated LT(S63K) developed by Rappuoli and colleagues (Pizza et al. 1994, Molecular Microbiology 14:51–60) and the second is the CT active-site mutant CT (S61F) developed by McGhee and colleagues (Yamamoto et al. 1997a, Proceedings of the National Academy of Sciences 94:5267–5272; Yamamoto et al. 1997b, Journal of Experimental Medicine 185:1203–1210). LT(S63K) was one of a group of LT A-subunit mutants shown to be devoid of biological activity on mouse Y-1 adrenal tumor cells and to lack detectable in vitro ADP-ribosyltransferase activity. LT(S63K) has been shown to be able to enhance production of anti-Ovalbumin (Ova) IgG in the sera and, to a lesser extent, anti-Ova IgA in vaginal secretions of mice immunized intranasally with up to five immunizations consisting of Ova combined with LT(S63K) (DiTommaso et al. 1996, Infection and Immunity 64:974–979). One publication (Partidos et al. 1996, Immunology 89:483–487) and a number of abstracts presented at various scientific meeting have further characterized this molecule as having intranasal adjuvanticity when administered with other antigens. Oral adjuvanticity for LT(S63K) has not been clearly established.

In two recent papers by Yamamoto et al. (Yamamoto et al. 1997a, Proceedings of the National Academy of Sciences 94:5267–5272; Yamamoto et al. 1997b, Journal of Experimental Medicine 185:1203–1210), mutants of CT with mutations in the NAD binding site that lack detectable in vitro ADP-ribosyltransferase activity and enterotoxicity and fail to induce cAMP accumulation in CHO cells were examined for parenteral and mucosal adjuvanticity. In the first study, these investigators demonstrated that CT(E112K) and CT(S61F) retained adjuvanticity for Ova when administered subcutaneously. CT-B alone did not function as an adjuvant, indicating that some portion of the A-subunit must be present for adjuvant activity. Both mutant CTs induced Ova specific CD4$^+$ T-cell proliferative responses with subsequent production of IL-4, IL-5, IL-6 and IL-10 (Th2 type cytokines) comparable to native CT. Significantly, neither native CT nor the mutant CTs promoted Th1 type cytokine development. Importantly, in these studies CT(E112K) exhibited adjuvant activity whereas LT(E112K) had previously been shown not to possess adjuvant activity (Lycke et al. 1992, European Journal of Immunology 22:2277–2281). One possible explanation for this difference in findings is that CT(E112K) was administered subcutaneously while LT(E112K) was administered orally. Alternatively, this may reflect inherent differences between CT and LT. In the second paper by Yamamoto et al., mice were immunized intranasally with CT(S61F) in conjunction with Ova, tetanus toxoid (TT), or influenza virus. Mice showed antigen-specific increases in serum antibodies as well as significant increases in antigen-specific antibodies in nasal and vaginal washes, saliva and fecal extracts that were comparable to those obtained with native CT. Again, CT-B failed to function as an adjuvant when administered intranasally. Both CT(S61F) and native CT elicited Th2 type cytokine secretion and cytokine mRNAs, but not Th1 type cytokine responses.

2.4. Mechanisms of Adjuvanticity

There are a number of potential cellular targets for these bacterially derived adjuvants and the precise mechanism of action remains to be determined. Clearly, significant efforts have been expended to resolve this (Bromander et al. 1993, Scandinavian Journal of Immunology 37:452–458; Cebra et al. 1986, In: Brown F, Channok R M, Lerner R A, editors. Vaccines 86: New approaches to immunization. Developing vaccines against parasitic, bacterial, and viral diseases: Cold Spring Harbor, N.Y. p 129–133; Clarke et al. 1991, Immunology 72:323–328; Clements et al. 1988, Vaccine 6:269–277; Elson 1989, Immunology Today 146:29–33; Elson and Ealding 1984a, Journal of Immunology 133:2892–2897; Elson and Ealding 1984b, Journal of Immunology 132:2736–2741; Elson et al. 1995, Journal of Immunology 154:1032–1040; Hornquist and Lycke 1993, European Journal of Immunology 23:2136–2143; Lycke et al. 1991; Nedrud and Sigmund 1991, Reg. Immunol. 3:217–222; Snider et al. 1994, Journal of Immunology 53:647–657; Takahashi et al. 1996, Journal of Infectious Diseases 173:627–635; Xu-Amano et al. 1994, Vaccine 12:903–911; Xu-Amano et al. 1993, Journal of Experimental Medicine 178:1309–1320). Several models have been proposed, none of which is completely satisfactory. A summary of these proposed mechanisms is found in the review by Freytag and Clements (Freytag and Clements, 1999, Curr Top Microbiol Immunol 236:215–36). Rather than a single defined mechanism, adjuvanticity should be viewed as an outcome and not an event. It is likely to be some combination of effects that collectively results in the observed outcome known as enhanced immunity or adjuvanticity. It is also important to note that most studies attempting to define the mechanism of adjuvanticity of CT and LT focus on induction of sIgA and Th2 events as the only or most relevant outcomes, ignoring the Th1 induction potential of LT which is likely to be important for protection against intracellular bacterial pathogens and viruses.

2.5. Role of cAMP in Adjuvanticity

The role of cAMP in the adjuvanticity of CT, LT, and mutants of CT and LT remains controversial, in part because different mutants of LT and CT have been evaluated using varying techniques in different laboratories and in part because different routes of administration (i.e., intranasal, oral) have been employed with various antigens. A recent report by Cheng et al. (Cheng et al. 1999, Vaccine 18(1–2): 38–49) provided a side-by-side comparison of LT, active-site mutants, the protease-site mutant LT(R192G), and recombinant B-subunit for the ability to induce specific, targeted immunologic outcomes using a single, defined antigen (Tetanus Toxoid) following two different mucosal routes of immunization (intranasal or oral). For this study, these investigators employed the Y-1 Adrenal Tumor Cell assay, a non-polarized Caco-2 cell assay for induction of cAMP, the Patent Mouse assay for enterotoxicity (Guidry et al., Infect. And Immun., 1997, 65(12):4943–4950), and an in vitro antigen restimulation assay on splenic mononuclear cells for determination of Th1 and Th2 type cytokine production. The Patent Mouse assay is a modification of the sealed adult mouse assay of Richardson et al. (Richardson et al. 1984, Infection and Immunity 43:482–486). It is slightly less sensitive than the more traditional Rabbit Ligated Ileal Loop assay, but responds to native LT and CT in a dose dependent fashion. In those studies, following intranasal immunization, both Th1 and Th2 type cellular immune responses to TT differed for the various active site mutants and LT-B and were dependent upon their ability to induce cAMP. For example, despite the fact that LT-B given intranasally can induce serum IgG, it is not able to induce any significant level of T cell response. Furthermore, while all active site mutants examined were able to induce antigen-specific antibody responses when administered intranasally, only native LT, LT(A69G), and LT(R192G), which retained the ability to induce production of cAMP, were able to elicit antigen-specific Th1 and Th2 cytokines following intranasal immunization in combination with TT. As with intranasal immunization, production of both Th1 and Th2-type cytokines following oral immunization was correlated with the ability to induce accumulation of cAMP.

Recently, Giuliani et al. (Giuliani et al. 1998, J Exp Med 187(7):1123–32) compared two active-site mutants, LT(S63K) and LT(A72R), for the ability to function as intranasal adjuvants. In those studies, LT(A72R) which retains some level of enzymatic activity was a better intranasal adjuvant for ovalbumin than LT(S63K) which those authors have reported to lack any detectable enzymatic activity. It remains to be seen whether LT(A72R) induces antigen-specific cytokine responses or functions orally in animals or humans.

Both CT and LT have significant potential to function as mucosal adjuvants for co-administered antigens and to facilitate the development of entire new classes of vaccines for-mucosal delivery. The data reported by Cheng et al. makes it clear that different mutants of LT have different properties that vary depending upon the nature of the mutation and the route of delivery. Specifically, those mutants that retain the ability to induce cAMP elicit quantitatively and qualitatively different responses than do those mutants that lack this function. For induction of antigen-specific antibody responses, it appears that any of the mutants examined in Cheng et al. will suffice if delivered intranasally. Clearly, the best cellular responses are elicited by native LT and mutants that retain some cAMP activity and only those that retain some cAMP activity can elicit Th1 type responses when administered orally. Significant serum antigen-specific IgG responses following oral administration were only observed for these mutants as well, and not for those that lacked the ability to induce cAMP.

2.6. Analysis of Hybrid Toxins

One recent study has employed hybrid toxins to explore the differential toxicity of CT and LT (Rodighiero et al. 1999, J Biol Chem 274(7):3962–9; Rodighiero et al. 1998, Biochem Soc Trans 26(4):S364). In those studies, hybrid toxins were constructed in which the A1 fragment of one toxin was substituted for that of the other (CT-A1:LT-A2$^{REDL}$/LT-B; LT-A1:CT-A2$^{KDEL}$/CT-B) as well as hybrids in which the putative ER-retention signal was altered (CT-A1:CT-A2$^{RDEL}$/CT-B; CT-A1:CT-A2$^{RDEL}$/LT-B). (Importantly, an LT-A/CT-B hybrid was neither created nor evaluated in these studies). The findings from these hybrid toxin studies are 1) CT-A1:LT-A2$^{REDL}$/LT-B is less potent than wild type CT at inducing chloride secretion; 2) LT-A1:CT-A2$^{KDEL}$/CT-B induced chloride secretion at levels comparable to levels induced by wild type CT; 3) all of the constructs containing CT-A1 had equivalent ADP-ribosyltransferase activity; 4) wild type LT and LT-A1:CT-A2$^{KDEL}$/CT-B had higher activity than native CT, and 5the differences between the toxicities of CT and LT are not a function of differences in the ER retention signals. The third hybrid, CT-A1:CT-A2$^{RDEL}$/LT-B, induced chloride secretion at levels equivalent to wild type CT.

One other hybrid toxin study has been reported (Takeda et al. 1981, Infect Immun 34(2) : 341–6). In that study, LT-A/CT-B and CT-A/LT-B hybrids were prepared by dissociation:re-association chromatography (i.e., the hybrids were not produced recombinantly from an organism designed to express LT-A and CT-B in the absence of LT-B and CT-A, but, instead, were prepared by isolating wild-type LT and CT holotoxin and dissociating said holotoxins into their substituent subunits and then reassembling a hybrid holotoxin by combining the CT-B subunits with the LT-A subunits). The hybrids were reported to have toxicity similar to that of the parent proteins from which the A subunits were derived.

Citation or identification of any reference in any section of this application shall not be construed as an admission that such reference is available as prior art to the present invention.

3. SUMMARY OF THE INVENTION

The present invention provides a composition comprising an LT-A/CT-B hybrid enterotoxin holotoxin, which holotoxin has immunologic adjuvant activity and is substantially less toxic than native E. coli heat-labile enterotoxin holotoxin as measured in the patent mouse assay.

Also provided is a composition useful in producing a protective immune response to a pathogen in a host comprising an admixture of an effective amount of an antigen and an adjuvant effective amount of a composition comprising an LT-A/CT-B hybrid enterotoxin holotoxin, which holotoxin has immunologic adjuvant activity and is substantially less toxic than native E. coli heat-labile enterotoxin holotoxin as measured in the patent mouse assay.

Also provided is a kit useful in producing a protective immune response in a host to a pathogen comprising two components: (a) an effective amount of antigen and (b) an adjuvant effective amount of an LT-A/CT-B hybrid enterotoxin holotoxin, which holotoxin has immunologic adjuvant activity and is substantially less toxic than native E. coli heat-labile enterotoxin holotoxin as measured in the patent mouse assay.

The present invention also provides a method of creating or sustaining a protective or adaptive immune response to an antigen in a host comprising administering an admixture of an effective amount of an antigen and an adjuvant effective amount of an LT-A/CT-B hybrid enterotoxin holotoxin, which holotoxin has immunologic adjuvant activity and is substantially less toxic than native E. coli heat-labile enterotoxin holotoxin as measured in the patent mouse assay, in an orally acceptable pharmaceutical carrier.

The present invention also provides a method of inducing a protective immune response to an antigen in a host comprising administering an effective amount of an antigen in conjunction with an adjuvant effective amount of an LT-A/CT-B hybrid enterotoxin holotoxin, which holotoxin has immunologic adjuvant activity and is substantially less toxic than native E. coli heat-labile enterotoxin holotoxin as measured in the patent mouse assay.

Also provided is a method of inducing a protective immune response against an enterotoxic bacterial organism comprising administering an adjuvant effective amount of an LT-A/CT-B hybrid enterotoxin holotoxin, which holotoxin has immunologic adjuvant activity and is substantially less toxic than native E. coli heat-labile enterotoxin holotoxin as measured in the patent mouse assay, as a component of a vaccine directed against the enterotoxic bacterial organism.

The present invention is based, in part, on the observation that a hybrid toxin molecule, designated LT-A/CT-B, consisting of the A-subunit of the heat labile toxin of Escherichia coli (LT-A) and the B-subunit of the cholera enterotoxin of Vibrio cholerae (CT-B) has significantly and unexpectedly reduced enterotoxicity and enzymatic activity when compared to either native LT or native CT and yet retains the adjuvant properties of native LT for induction of humoral and cellular immune responses to a co-administered antigen. These findings are in contrast to the findings of Takeda et al. (Takeda et al. 1981, Infect Immun 34(2):341–6) in which hybrid toxin molecules were found to have toxicity equivalent to the parent proteins from which the A-subunits were generated, and the findings of Rodighiero et al. (Rodighiero et al. 1999, J Biol Chem 274(7):3962–9; Rodighiero et al. 1998, Biochem Soc Trans 26(4):S364) in which a hybrid, LT-A1:CT-A2$^{KDEL}$/CT-B, induced chloride secretion at levels comparable to levels induced by wild type CT. In neither of those studies was adjuvanticity of the hybrid molecules examined. Indeed, based upon these published findings (Rodighiero et al. 1999, J Biol Chem 274(7):3962–9; Rodighiero et al. 1998, Biochem Soc Trans 26(4):S364; Takeda et al. 1981, Infect Immun 34(2):341–6), one skilled in the art would predict that LT-A/CT-B would retain full enzymatic activity and enterotoxicity.

The reduction in enzymatic activity and toxicity of the present novel hybrid LT-A/CT-B when compared with native LT and native CT is also surprising in that it is not necessary to mutate or alter the A-subunit of the holotoxin. Previous studies have shown that alteration, by site-directed mutagenesis, of amino acids in CT or LT involved in NAD-binding and catalysis alters ADP-ribosyltransferase activity with a corresponding loss of toxicity in a variety of biological assay systems (Burnette et al. 1991; Fontana et al. 1995, Infection and Immunity 63:2356–2360; Harford et al. 1989, European Journal of Biochemistry 183:311–316; Hase et al. 1994, Infection and Immunity 62:3051–3057; Lobet et al. 1991, Infection and Immunity 59:2870–2879; Lycke et al. 1992, European Journal of Immunology 22:2277–2281; Merritt et al. 1995, Nature Structural Biology 2:269–272; Moss et al. 1993, Journal of Biological Chemistry 268:6383–6387; Pizza et al. 1994, Molecular Microbiology 14:51–60; Tsuji et al. 1991, FEBS Letters 291:319–321; Tsuji et al. 1990, Journal of Biological Chemistry 265:22520–22525; Yamamoto et al. 1997a, Proceedings of the National Academy of Sciences 94:5267–5272; Yamamoto et al. 1997b, Journal of Experimental Medicine 185:1203–1210). The LT-A/CT-B hybrid that is one embodiment of the current invention has an unaltered LT-A subunit and therefore there is no reason, a priori, for one to expect the LT-A/CT-B hybrid to have reduced enzymatic activity or enterotoxicity. Indeed, the contrasting, inverse hybrid CT-A/LT-B has undiminished toxicity and enzymatic activity when compared to native LT and CT.

With respect to adjuvanticity, despite the significant and surprising reduction in enterotoxicity and enzymatic activity, the novel hybrid of the present invention retains the ability to function as a mucosal adjuvant for a co-administered antigen.

LT-A/CT-B hybrids in which the A subunit is a mutant subunit, for example, LT-A(R192G), have even further reduced toxicity when compared to the non-hybrid LT-A (R192G)/LT-B holotoxin. Thus, a further object of the present invention is to reduce the toxicity of any LT-A molecule, either wild-type or mutant, by providing a hybrid holotoxin comprising the mutant LT-A and CT-B.

The present invention provides a method for reducing the enterotoxic potential of LT and CT, thereby providing a safety window for use of these molecules as immunologic adjuvants.

The invention also provides a composition useful in these methods. The composition comprises an effective amount of LT-A/CT-B in combination with an effective amount of antigen.

Also provided are methods of using LT-A/CT-B as an adjuvant for the stimulation of an immune response against an antigen administered in combination with the novel adjuvant.

4. BRIEF DESCRIPTION OF THE FIGURES

The present invention may be understood more fully by reference to the following detailed description of the invention, examples of specific embodiments of the invention and the appended figures in which:

FIG. 1 is a schematic diagram of the plasmid pLT-A/CT-B, which encodes LT-A and CT-B under the control of the lac promoter and also depicts plasmid pCT-A/LT-B which encodes CT-A and LT-B under the control of the lac promoter. FIG. 1 also depicts the sequences used to construct pLT-A/CT-B and pCT-A/LT-B, a key for said sequences follows:

| | |
|---|---|
| pBB6 | 5.1 kb PstI-EcoRI fragment of plasmid pBB6 containing intact ctx and zot genes cloned into pBR322 |
| pCT2 | 5.1 kb PstI-EcoRI fragment of plasmid pCT2 containing intact ctx and zot genes cloned into pUC19 |
| pCTA3 | 1 kb Eco-RI-SstI fragment subcloned from pCT2 into pUC18 following PCR introduction of EcoRI and SstI restriction sites upstream and downstream, respectively, of ctxa and ctxb. |

-continued

| | |
|---|---|
| pCS96 | 1.5 kb EcoRI-HindIII fragment of plasmid pCS96 containing intact ltx genes cloned into pUC18. |
| pCT-A/LT-B | 1.5 kb EcoRI-HindIII fragment of plasmid pCT-A/LT-B containing intact ctxa and ltxb genes cloned into pUC18. |
| pCTB5 | Sst-EcoRI fragment subcloned from pCT2 and pUC18 following PCR introduction of SstI restriction site upstream of ctxb. |
| pLT-A/CT-B | 1.5 kb EcoRI-HindIII fragment of plasmid pLT-A/CT-B containing intact ltxa and ctxb genes cloned into pUC18. |

FIG. 2 is a graphical representation of results from a patent mouse intestinal assay demonstrating that LT-A/CT-B and LT-A(R192G)/CT-B have reduced enterotoxicity when compared to native LT, CT, LT(R192G) or CT-A/LT-B, and that LT-A(R192G)/CT-B has reduced toxicity when compared to LT-A/CT-B. Groups of mice were orally inoculated with LT, CT, CT-A/LT-B, or LT-A/CT-B at 5, 25, or 125 μg. Following a three hour interval, the gut:carcass ratio of each animal was determined. The gut-carcass ratio is defined as the intestinal weight divided by the remaining carcass weight. There were three animals per group and the means for each data point are shown.

FIG. 3 depicts the results of a cAMP assay demonstrating that LT-A/CT-B has significantly reduced enzymatic activity when compared to native LT, CT, or CT-A/LT-B.

FIG. 4 depicts a comparison of the abilities of LT-A/CT-B, native LT, native CT, and CT-A/LT-B to induce antigen-specific antibody responses following mucosal immunization with Tetanus Toxoid in conjunction with either LT-A/CT-B, native LT, native CT, or CT-A/LT-B. LT-A/CT-B was as effective as native LT, native CT, or CT-A/LT-B in inducing antigen-specific antibody responses in immunized animals, despite the significantly reduced enterotoxicity and enzymatic activity of LT-A/CT-B when compared to native LT, native CT, or CT-A/LT-B.

FIG. 5 depicts the results of a comparison of LT-A/CT-B with native LT, native CT, and CT-A/LT-B for their ability to enhance production of antigen-specific Th1-type cytokines; specifically, IFN-gamma, by mononuclear cells from the spleens of immunized animals. LT-A/CT-B was as effective as native LT, and more effective than native CT, or CT-A/LT-B in inducing antigen-specific IFN-gamma in immunized animals, despite the significantly reduced enterotoxicity and enzymatic activity of LT-A/CT-B when compared to native LT, native CT, or CT-A/LT-B.

FIG. 6 depicts a comparison of LT-A/CT-B with native LT, native CT, and CT-A/LT-B for the ability to enhance production of antigen-specific Th2-type cytokines; specifically, IL-6, by monbnuclear cells from the spleens of immunized animals. LT-A/CT-B was more effective than native LT, native CT, or CT-A/LT-B in inducing antigen-specific IL-6 in immunized animals, despite the significantly reduced enterotoxicity and enzymatic activity of LT-A/CT-B when compared to native LT, native CT, or CT-A/LT-B.

5. DETAILED DESCRIPTION OF THE INVENTION

The present invention encompasses a composition and methods for its use to promote the production of serum and/or mucosal antibodies as well as cell-mediated immune responses against antigens that are simultaneously administered with a hybrid bacterial toxin. The hybrid toxin combines the A-subunit of the heat-labile enterotoxin of *Escheri-* chia coli (LT-A) with the B-subunit of the cholera enterotoxin of *Vibrio cholerae* (CT-B). This hybrid molecule has unexpectedly reduced enterotoxicity and enzymatic activity yet retains its ability to act as an immunological adjuvant. The invention is based, in part, on the discovery that LT-A/CT-B has utility as an adjuvant. LT-A/CT-B can be administered in any manner known to those of skill in the art, preferably by mucosal, for example but not limited to oral, administration. The mode of administration may be mucosal (i.e., intranasal, oral, rectal) or parenteral (i.e., subcutaneous, intramuscular, intradermal, intravenous, intraperitoneal). Administration results in the production of antibodies as well as cell-mediated immune responses against the antigens with which LT-A/CT-B is delivered.

Hybrids consisting of the A-subunit of one toxin combined with the B-subunit of the other toxin were constructed. It was unexpectedly found that LT-A/CT-B has significantly reduced enterotoxicity in the patent mouse assay when compared to native LT, native CT, or the alternate hybrid CT-A/LT-B. In order to more fully evaluate this unexpected finding, LT-A/CT-B was evaluated for the ability to induce cAMP in cultured Caco2 cells. Activity in this assay has been shown to be directly correlated with the toxicity of these molecules. Despite having an unaltered, intact A-subunit, the hybrid molecule LT-A/CT-B induced significantly less cAMP in this assay when compared to native LT, native CT, or the alternate hybrid CT-A/LT-B.

As described above, an unexpected finding was that LT-A/CT-B has significantly reduced toxicity and enzymatic activity despite having an unmodified LT-A subunit. Also, surprisingly, even when the LT-A subunit is modified (for example, when the LT-A subunit has an R192G mutation), the hybrid LT-A/CT-B has even less toxicity than the non-hybrid LT with that same mutation, e.g., LT-A(R192G)/CT-B has reduced toxicity as compared to LT-A(R192G)/LT-B. Thus, the present invention also encompasses LT-A/CT-B hybrid toxins, wherein the LT-A subunit, the CT-B subunit, or both subunits of the hybrid toxin are mutant subunits, e.g., differing from wild-type subunits by one or more amino acid substitutions, deletions or additions. Suitable mutant LT-A subunits include LT-A(R192G), LT-A(R192G/L211A), LT-A(S63K), LT-A(E112K), LT-A(Δ192–194), LT-A(A69G) and LT-A(A72R). The use of hybrids containing mutant, detoxified LT-A subunits provides the advantage of two separate means for reducing the toxicity of the LT-A/CT-B hybrid. The mutation of LT-A alone renders the molecule safe for administration; when combined with CT-B to form a hybrid, the resulting molecule can be even less toxic because both the mutation of LT-A and the association of LT-A with CT-B reduce toxicity. In addition, the use of mutant CT-B subunits is also-encompassed.

The present invention supersedes the prior art in that LT-A/CT-B retains adjuvanticity for induction of antigen-specific antibody and cell mediated immune responses against a co-administered antigen. In the illustrative example presented in section 6, LT-A/CT-B induces antigen-specific Th1 type responses equivalent to those induced by native LT and significantly greater than those induced by native CT or the alternate hybrid CT-A/LT-B. Furthermore, LT-A/CT-B induces antigen-specific Th2 type responses greater than those induced by native LT, native CT or the alternate hybrid CT-A/LT-B.

The present invention also provides a method of producing LT-A/CT-B comprising the steps of
 a) culturing a cell comprising a vector capable of expressing in said cell an LT-A subunit and culturing a cell comprising a vector capable of expressing in said cell a CT-B subunit, but not capable of expressing an LT-B subunit or a CT-A subunit under conditions that allow for the expression by said cell or cells of said LT-A and CT-B molecules, and
 b) isolating the LT-A/CT-B produced by the cell or cells.

It will be apparent to the skilled artisan that both subunits may be produced in one cell from one vector, or in one cell from two different vectors, or in different cells from two different vectors.

Preferably the cell is a bacterial cell, most preferably an *E. coli* cell, and the vector is a plasmid.

Variations of this method include separate expression and isolation of the LT-A and CT-B subunits from different cell cultures and subsequent association of said subunits to form LT-A/CT-B, and methods wherein the LT-A subunit, the CT-B subunit, or both subunits are mutant subunits.

5.1 Production of LT-A/CT-B

LT-A/CT-B can be produced by a number of means apparent to those of skill in the art. For example, plasmid pLT-A/CT-B, fully described in Example 6.1, can be utilized to produce substantially pure LT-A/CT-B in *E. coli*. LT-A/CT-B can be isolated by agarose affinity chromatography from bacteria expressing an LT-A/CT-B encoding plasmid. Alternate methods of purification will be apparent to those skilled in the art.

The LT-A/CT-B of the present invention is preferably isolated LT-A/CT-B. As used herein, an "isolated" LT-A/CT-B means LT-A/CT-B separated from that which it is normally associated, or separated from the material normally present during the production of LT-A/CT-B by a cell. More preferably, the LT-A/CT-B is substantially purified, i.e., LT-A/CT-B is 5%, 20%, 30%, 40%, 50%, 60%, 70%, 80%, 90%, 95% or 99% of the total protein present in an LT-A/CT-B comprising preparation.

5.2 Mode of Administration of LT-A/CT-B and Unrelated Antigens

In accordance with the present invention, LT-A/CT-B can be administered in conjunction with any biologically relevant antigen and/or vaccine, such that an increased immune response, as compared to the immune response achieved by administration of said antigen and/or vaccine without LT-A/CT-B, to said antigen and/or vaccine is achieved. In a preferred embodiment, LT-A/CT-B and antigen are administered simultaneously in a pharmaceutical composition comprising an effective amount of LT-A/CT-B and an effective amount of antigen. The mode of administration is mucosal (i.e., intranasal, oral, rectal) or parenteral (i.e., subcutaneous, intramuscular, intradermal, intravenous, intraperitoneal). The respective amounts of LT-A/CT-B and antigen will vary depending upon the identity of the route of administration, antigen employed and the species of animal to be immunized. In one embodiment, the initial administration of LT-A/CT-B and antigen is followed by a boost of the relevant antigen. In another embodiment no boost is given. The timing of boosting may vary, depending on the route, antigen and the species being treated. The modifications in route, dosage range and timing of boosting for any given species and antigen are readily determinable by routine experimentation. The boost may be of antigen alone or in combination with LT-/CT-B.

The methods and compositions of the present invention are intended for use both in immature and mature vertebrates, in particular birds and mammals, including but not limited to humans. Useful antigens, as examples and not by way of limitation, include antigens from pathogenic strains of bacteria (*Streptococcus pyogenes, Streptococcus*

*pneumoniae, Neisseria gonorrhoeae, Neisseria meningitidis, Corynebacterium diphtheriae, Clostridium botulinum, Clostridium perfringens, Clostridium tetani, Haemophilus influenzae, Klebsiella pneumoniae, Klebsiella ozaenae, Klebsiella rhinoscleromatis, Staphylococcus aureus, Vibrio cholerae, Escherichia coli, Pseudomonas aeruginosa, Campylobacter jejuni, Aeromonas hydrophila, Bacillus cereus, Edwardsiella tarda, Yersinia enterocolitica, Yersinia pestis, Yersinia pseudotuberculosis, Shigella dysenteriae, Shigella flexneri, Shigella sonnei, Salmonella typhimurium, Treponema pallidum, Treponema pertenue, Treponema carateneum, Borrelia vincentii, Borrelia burgdorferi, Leptospira icterohemorrhagiae, Mycobacterium tuberculosis, Toxoplasma gondii, Pneumocystis carinii, Francisella tularensis, Brucella abortus, Brucella suis, Brucella melitensis, Mycoplasma spp., Rickettsia prowazeki, Rickettsia tsutsugamushi, Chlamydia spp., Helicobacter pylori*); pathogenic fungi (*Coccidioides immitis, Aspergillus fumigatus, Candida albicans, Blastomyces dermatitidis, Cryptococcus neoformans, Histoplasma capsulatum*); protozoa (*Entamoeba histolytica, Trichomonas tenas, Trichomonas hominis, Trichomonas vaginalis, Trypanosoma gambiense, Trypanosoma rhodesiense, Trypanosoma cruzi, Leishmania donovani, Leishmania tropica, Leishmania braziliensis, Pneumocystis pneumonia, Plasmodium vivax, Plasmodium falciparum, Plasmodium malaria*); or Helminths (*Enterobius vermicularis, Trichuris trichiura, Ascaris lumbricoides, Trichinella spiralis, Strongyloides stercoralis, Schistosoma japonicum, Schistosoma mansoni, Schistosoma haematobium*, and hookworms) either presented to the immune system in whole cell form or in part isolated from media cultures designed to grow said organisms which are well know in the art, or protective antigens from said organisms obtained by genetic engineering techniques or by chemical synthesis.

Other relevant antigens would be from pathogenic viruses (as examples and not by limitation: Poxviridae, Herpesviridae, Herpes Simplex virus 1, Herpes Simplex virus 2, Adenoviridae, Papovaviridae, Enteroviridae, Picornaviridae, Parvoviridae, Reoviridae, Retroviridae, influenza viruses, parainfluenza viruses, mumps, measles, respiratory syncytial virus, rubella, Arboviridae, Rhabdoviridae, Arenaviridae, Hepatitis A virus, Hepatitis B virus, Hepatitis C virus, Hepatitis E virus, Non-A/Non-B Hepatitis virus, Rhinoviridae, Coronaviridae, Rotoviridae, and Human Immunodeficiency Virus) either presented to the immune system in whole or in part isolated from media cultures designed to grow such viruses which are well known in the art or protective antigens therefrom obtained by genetic engineering techniques or by chemical synthesis.

Further examples of relevant antigens include, but are not limited to, vaccines. Examples of such vaccines include, but are not limited to, influenza vaccine, pertussis vaccine, diphtheria and tetanus toxoid combined with pertussis vaccine, hepatitis A vaccine, hepatitis B vaccine, hepatitis C vaccine, hepatitis E vaccine, Japanese encephalitis vaccine, herpes vaccine, measles vaccine, rubella vaccine, mumps vaccine, mixed vaccine of measles, mumps and rubella, papillomavirus vaccine, parvovirus vaccine, respiratory syncytial virus vaccine, Lyme disease vaccine, polio vaccine, malaria vaccine, varicella vaccine, gonorrhea vaccines schistosomiasis vaccine, rotavirus vaccine, mycoplasma vaccine pneumococcal vaccine, meningococcal vaccine, *Campylobacter* vaccine, *Helicobacter* vaccine, cholera vaccine, enterotoxigenic *E. coli* vaccine, enterohemorrhagic *E. coli* vaccine, *Shigella* vaccine, *Salmonella* vaccine and others. These can be produced by known common processes. In general, such vaccines comprise either the entire organism or virus grown and isolated by techniques well known to the skilled artisan or comprise relevant antigens of these organisms or viruses which are produced by genetic engineering techniques or chemical synthesis. Their production is illustrated by, but not limited to, as follows:

Influenza vaccine: a vaccine comprising the whole or part of hemagglutinin, neuraminidase, nucleoprotein and matrix protein which are obtainable by purifying a virus, which is grown in embryonated eggs, with ether and detergent, or by genetic engineering techniques or chemical synthesis.

Pertussis vaccine: a vaccine comprising the whole or a part of pertussis toxin, hemagglutinin and K-agglutinin which are obtained from avirulent toxin with formalin which is extracted by salting-out or ultracentrifugation from the culture broth or bacterial cells of *Bordetella pertussis*, or by genetic engineering techniques or chemical synthesis.

Diphtheria and tetanus toxoid combined with pertussis vaccine: a vaccine mixed with pertussis vaccine, diphtheria and tetanus toxoid.

Japanese encephalitis vaccine: a vaccine comprising the whole or part of an antigenic protein which is obtained by culturing a virus intracerebrally in mice and purifying the virus particles by centrifugation or ethyl alcohol and inactivating the same, or by genetic engineering techniques or chemical synthesis.

Hepatitis B vaccine: a vaccine comprising the whole or part of an antigen protein which is obtained by isolating and purifying the HBs antigen by salting-out or ultracentrifugation, obtained from hepatitis carrying blood, or by genetic engineering techniques or by chemical synthesis.

Measles vaccine: a vaccine comprising the whole or part of a virus grown in a cultured chick embryo cells or embryonated egg, or a protective antigen obtained by genetic engineering or chemical synthesis.

Rubella vaccine: a vaccine comprising the whole or part of a virus grown in cultured chick embryo cells or embryonated egg, or a protective antigen obtained by genetic engineering techniques or chemical synthesis.

Mumps vaccine: a vaccine comprising the whole or part of a virus grown in cultured rabbit cells or embryonated egg, or a protective antigen obtained by genetic engineering techniques or chemical synthesis.

Mixed vaccine of measles, rubella and mumps: a vaccine produced by mixing measles, rubella and mumps vaccines.

Rotavirus vaccine: a vaccine comprising the whole or part of a virus grown in cultured MA 104 cells or isolated from the patient's feces, or a protective antigen obtained by genetic engineering techniques or chemical synthesis.

Mycoplasma vaccine: a vaccine comprising the whole or part of mycoplasma cells grown in a liquid culture medium for mycoplasma or a protective antigen obtained by genetic engineering techniques or chemical synthesis.

Those conditions for which effective prevention may be achieved by the present method will be obvious to the skilled artisan.

The vaccine preparation compositions of the present invention can be prepared by mixing the above illustrated antigens and/or vaccines with LT-A/CT-B at a desired ratio. Pyrogens or allergens should naturally be removed as completely as possible. The antigen preparation of the present invention can be used by preparing the antigen per se and the LT-A/CT-B separately or together.

Further, the present invention encompasses a kit comprising an effective amount of antigen and an adjuvant effective amount of LT-A/CT-B. In use, the components of the kit can either first be mixed together and then administered or the components can be administered separately within a short time of each other.

The vaccine preparation compositions of the present invention can be combined with either a liquid or solid pharmaceutical carrier, and the compositions can be in the form of tablets, capsules, powders, granules, suspensions or solutions. The compositions can also contain suitable preservatives, coloring and flavoring agents, or agents that produce slow release. Potential carriers that can be used in the preparation of the pharmaceutical compositions of this invention include, but are not limited to, gelatin capsules, sugars, cellulose derivations such as sodium carboxymethyl cellulose, gelatin, talc, magnesium stearate, vegetable oil such as peanut oil, etc., glycerin, sorbitol, agar and water. Carriers may also serve as a binder to facilitate tabletting of the compositions for convenient administration.

6. EXAMPLES

The following examples are presented for purposes of illustration only and are not intended to limit the scope of the invention in any way.

6.1. Production of Hybrid Toxins

For construction of some plasmids, new restriction enzyme cleavage sites were introduced by site-directed mutagenesis to facilitate subcloning of gene fragments. Oligonucleotide primers used for this purpose, and for the amplification of CT-A from pCT2, are detailed below. Hybrid plasmids were verified by sequencing.

Construction of the CT-A/LT-B Hybrid

A hybrid plasmid containing the wild type CT, designated pCT2, was created by subcloning a 5.1 kb fragment from the plasmid pBB6, which contains both the zot and ctx genes from the classical Inaba V. cholerae strain 569B, (a generous gift from J. Kaper) into pUC19. PCR was performed with primers designed to amplify the ctxa gene using pCT2 as a template (primers 1 and 2, listed below). PCR product was digested with EcoR1 and SstI, which cleaved restriction sites at the ends of ctxa introduced by the PCR primers, and ligated into pUC18 to create pCTA3. A gene fragment encoding LT-B from pCS96, a pUC18 based plasmid containing the LT operon (International Patent Publication WO99/47164, International Patent Publication WO99/47165), was then introduced by restriction digest with Sst and HindIII, yielding a CT-A/LT-B construct.

Construction of the LT-A/CT-B Hybrid pCT2 was mutagenized to introduce a new SstI site at the end of the ctxa gene which parallels an existing site in the LT gene (primers 2 and 3). A restriction digest with SstI and HindIII released the ctxb gene, which is then ligated into pUC18 to form pCTB5. PCS96 was digested with SstI to release a fragment containing the lta gene, which was then ligated into SstI-digested pCTB5, producing an LT-A/CT-B construct. Attempts to purify CT from a plasmid containing the introduced SstI site, which changed a threonine to an alanine in the B subunit, proved problematic. The alanine was changed back to the wild type threonine in both the CT expressing plasmid and the pLT-A/CT-B plasmid (primers 4, 5,6 and 7)

Construction of Mutants

The various mutations described above were introduced using the QuickChange site-directed mutagenesis kit (Stratagene). The oligonucleotide primers used are shown below. Pfu DNA polymerase is used in the PCR reaction to extend primers and replicate the plasmid template. After completion of the reaction, samples are treated with DpnI, which selectively digests the parental DNA template based on dam methylation. The remaining DNA samples were then transformed into E. coli XL-1 Blue supercompetent cells and then into E. coli JM83 ara Δlac-proAB rpsLφ80δlacZ ΔM15 for expression and protein purification. Each mutation was confirmed by DNA sequencing.

```
Primer 1                                   (SEQ ID NO:1)
5'-GGCTGTGGGTAGAATTCAAACGGGG-3'

Primer 2                                   (SEQ ID NO:2)
5'-GAGGAGCTCCATGTGCATATGCTG-3'

Primer 3                                   (SEQ ID NO:3)
5'-CAGCAATATGCACATGGAGCTCCTC-3'

Primer 4                                   (SEQ ID NO:4)
5'-CAGCATATGCACATGGAACACCTC-3'

Primer 5                                   (SEQ ID NO:5)
5'-GAGGTGTTCCATGTGCATATGCTG-3'

Primer 6                                   (SEQ ID NO:6)
5'-CCTCTCTATGTGCATACGGAACACCTC-3'

Primer 7                                   (SEQ ID NO:7)
5'-GAGGTGTTCCGTATGCACATAGAGAGC-3'

Primer 8                                   (SEQ ID NO:8)
5'-CCGGGTTGTGGGAATGCTCCAGGATCCTCGATCAG-3'
```

Purification of Hybrid Toxins

All toxins were purified from cultures grown overnight in a 10 liter fermenter of Evan's medium supplemented with 100 μg of ampicillin per ml. The cells were harvested by centrifugation, resuspended in TEAN (0.2 M NaCl, 0.05 M Tris, 0.001 M EDTA, 0.003 M NaN3, pH 7.5), lysed by French press. Cell lysate was dialyzed against TEAN overnight at 4° C., clarified by centrifugation, and subjected to chromatography on designated immobilized D-galactose (Acros Organics, Fisher) in TEAN. Each purified toxin was characterized by SDS-PAGE.

6.2. LT-A/CT-B Exhibits Reduced Enterotoxicity

In order to evaluate the enterotoxicity of these hybrids, a patent mouse assay was performed wherein groups of mice were orally inoculated with CT, LT, LT(R192G), LT-A (R192G)/CT-B, CT-A/LT-B, or LT-A/CT-B at 5, 25, or 125 μg (50 and 250 μg in the cases of LT(R192G) and LT-A (R192G)/CT-B).

For the patent mouse cell assay, mice (in triplicate) were inoculated with the indicated compounds after being deprived of food the previous night. The mice were sacrificed after three hours by $CO_2$ inhalation. The entire intestine from duodenum to anus was then carefully removed to retain any accumulated fluid; residual mesentary was removed prior to weighing. The carcass was weighed separately, and a gut to carcass ratio was calculated for each animal.

Figure 1:
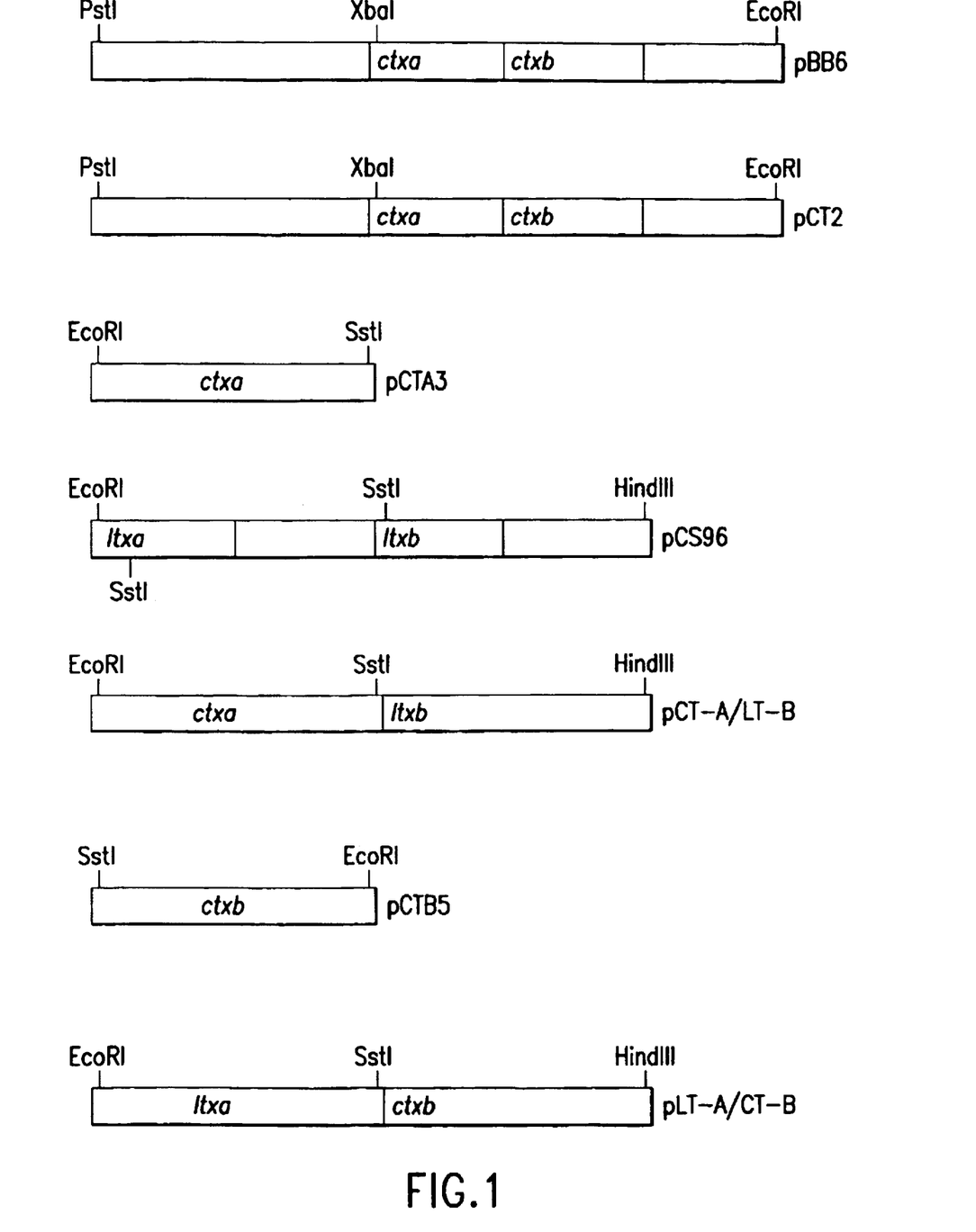
Figure 2:
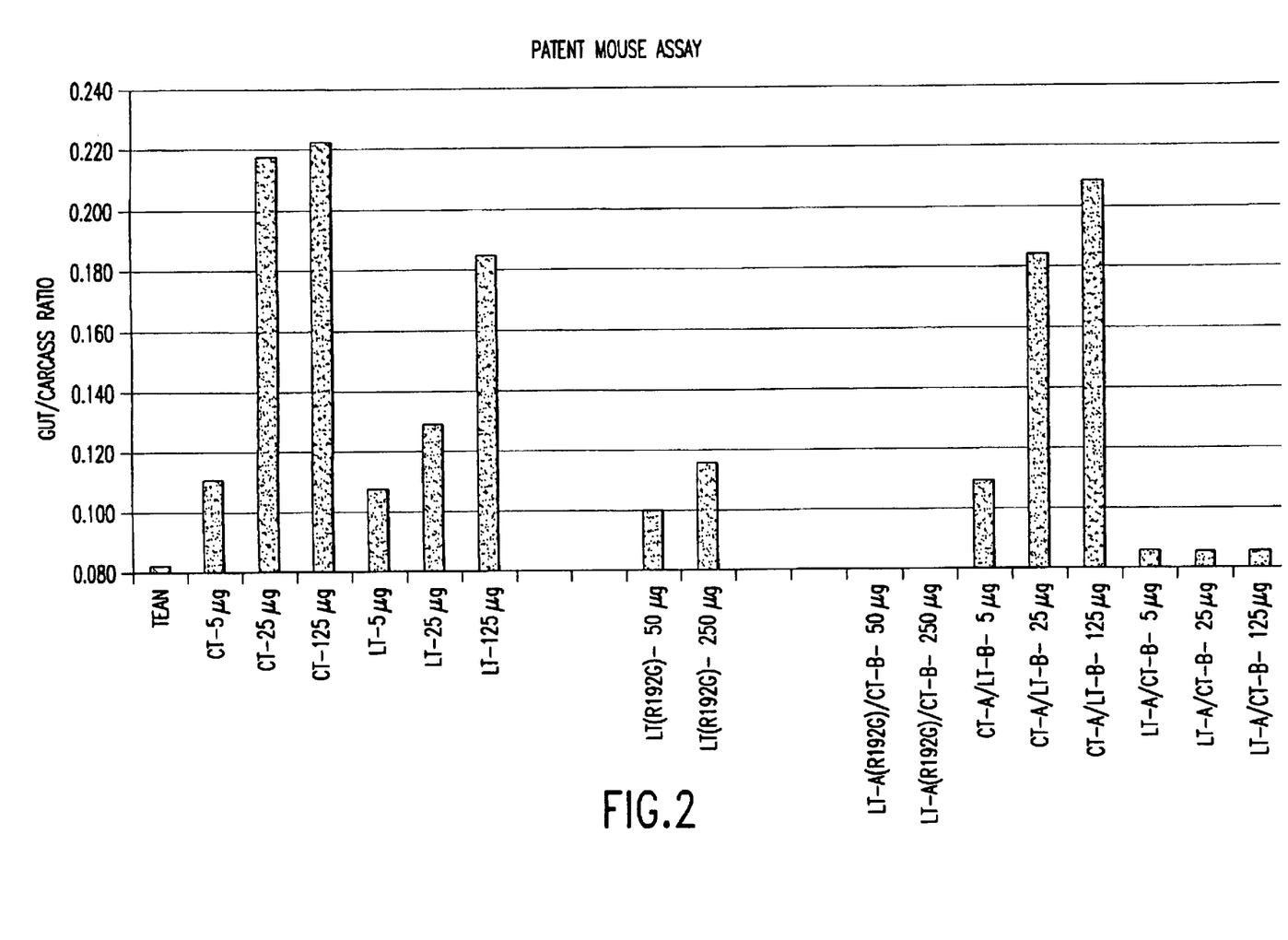

Based on the previous findings of others, it was anticipated that LT-A/CT-B and CT-A/LT-B would have undiminished enterotoxicity when compared to native LT and native CT since the A-subunits of the hybrid toxins were unaltered. As shown in FIG. 2, it was unexpectedly found that LT-A/CT-B and LT-A(R192G)/CT-B have significantly reduced enterotoxicity in the patent mouse assay when compared to native LT, native CT, LT(R192G) or the alternate hybrid CT-A/LT-B, and that LT-A(R192G)/CT-B has reduced toxicity with respect to LT-A/CT-B.

6.3. LT-A/CT-B Exhibits Reduced Enzymatic Activity

In order to more fully evaluate this unexpected finding, LT-A/CT-B was evaluated for the ability to induce cAMP in cultured Caco2 cells. Intracellular cAMP accumulation was determined as described by Grant et al. (Grant et al. 1994, Infection and Immunity 62:4270–4278). Cells are seeded in 6 well cluster plates (Corning Costar, Cambridge, MA) and grown to near confluence. Prior to addition of toxins, cells are incubated in MEM containing 1% FBS and 1 mM 3-isobutyl-1-methylxanthine (IBMX) (Sigma) for 30 minutes at 37° C. in 5% $CO_2$. One μg of each trypsin-cleaved toxin is added to each well of cells. At 1, 2, 3, and 4 hours after toxin addition, cells are washed twice with cold PBS. Intracellular cAMP is extracted by adding 0.4 mL of 0.1 N HCl to each well and incubating at room temperature for 15 minutes. cAMP is detected using an ELISA based low pH cAMP kit (R&D Systems, Minneapolis, Minn.) Activity in this assay has been shown to be directly correlated with the toxicity of these molecules.

Figure 3:
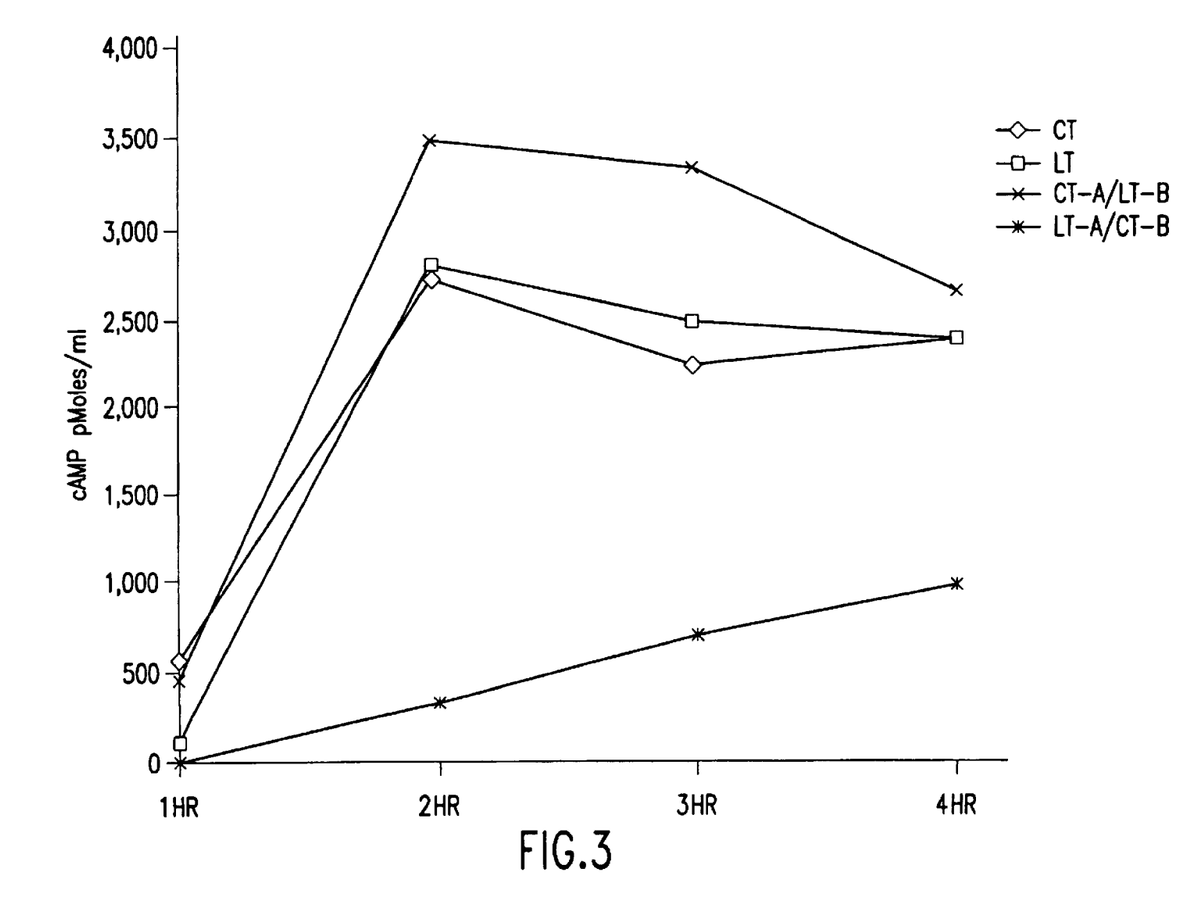

As shown FIG. 3, despite having an unaltered, intact A-subunit, the hybrid molecule LT-A/CT-B induced significantly less cAMP in this assay when compared to native LT, native CT, or the alternate hybrid CT-A/LT-B.

6.4. LT-A/CT-B Exhibits Adjuvanticity

Comparison of LT-A/CT-B with native LT, native CT, and CT-A/LT-B for the ability to induce antigen-specific serum IgG following mucosal immunization with Tetanus Toxoid in conjunction with either LT-A/CT-B, native LT, native CT, or CT-A/LT-B was conducted as follows. Groups of BALB/c mice were immunized intranasally once per week for three weeks. Intranasal immunization consists of 8 μl of the antigen preparation, (10 μg of TT with 5 μg of adjuvant). Eight μl aliquots were introduced into one nostril while the mice were under light anesthesia. One week after the third immunization, animals were sacrificed, serum was obtained by cardiac puncture and spleens were collected for T cell in vitro antigen restimulation assay.

Figure 4:
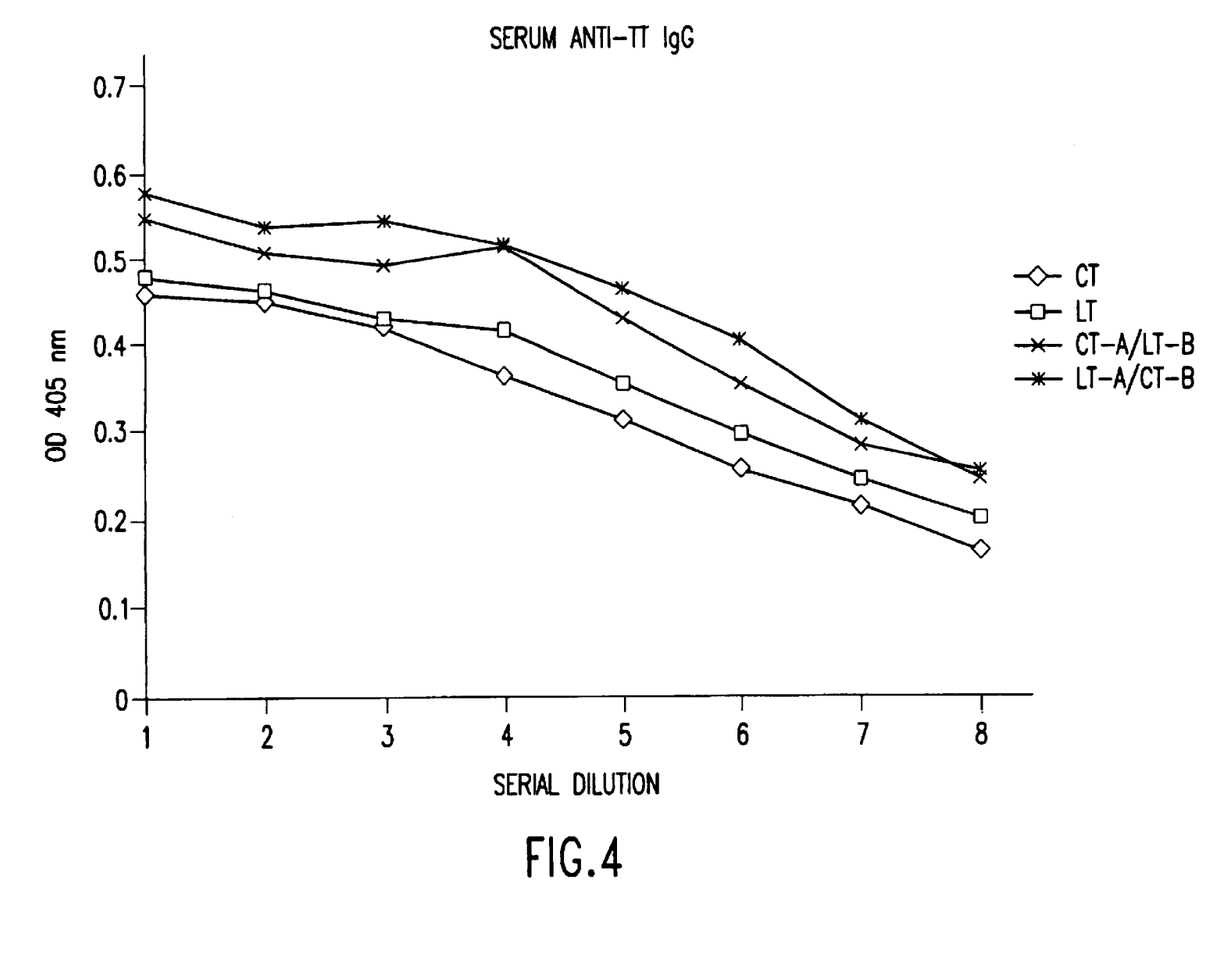

Antigen-specific antibody responses were determined by ELISA. Reagents and antisera for the ELISA were obtained from Sigma unless indicated otherwise. Serum samples were serially diluted 1:2 in PBS-0.05% Tween 20 and added to 96-well plates precoated with 10 μg of TT per well. Anti-TT IgG levels were determined with rabbit antiserum against mouse IgG conjugated to alkaline phosphatase. Reactions were stopped with 3 N NaOH, and the absorbance at 405 nm determined spectrophotometrically. Concentrations of IgG were determined using a standard curve generated with purified mouse myeloma proteins. As shown in FIG. 4, LT-A/CT-B was as effective as native LT, native CT, or CT-A/LT-B in inducing antigen-specific antibody responses in immunized animals, despite the significantly reduced enterotoxicity and enzymatic activity of LT-A/CT-B when compared to native LT, native CT, or CT-A/LT-B.

For in vitro antigen restimulation assays, BALB/c mice immunized as described above were sacrificed, and the spleens removed and pooled for each group. Spleens were homogenized through a cell dissociation sieve (Sigma), pelleted and resuspended in RPMI 1640 with 1% fetal bovine serum (FBS). Mononuclear cells were purified by gradient density centrifugation using Histopaque-1119 (Sigma), washed and resuspended in complete RPMI 1640 containing 10% FBS, 100 μg streptomycin sulfate and 0.25 μg amphotericin B (Gibco BRL), and 100 units penicillin G sodium per ml. Purified mononuclear cells were enumerated and tested for viability by Trypan blue exclusion. $1\times10^7$ mononuclear cells were added to each well in a 12 well plate containing $1\times10^6$ cells per well of incomplete Freund's adjuvant-elicited peritoneal macrophages obtained from naive mice and incubated with the antigen for an hour prior to addition of mononuclear cells. One, three, and five days post culture, supernatants were collected and kept at −20 C. until assayed. Cytokines in the culture supernatants were detected by murine ELISA kits (PharMingen San Diego, Calif.).

Figure 5:
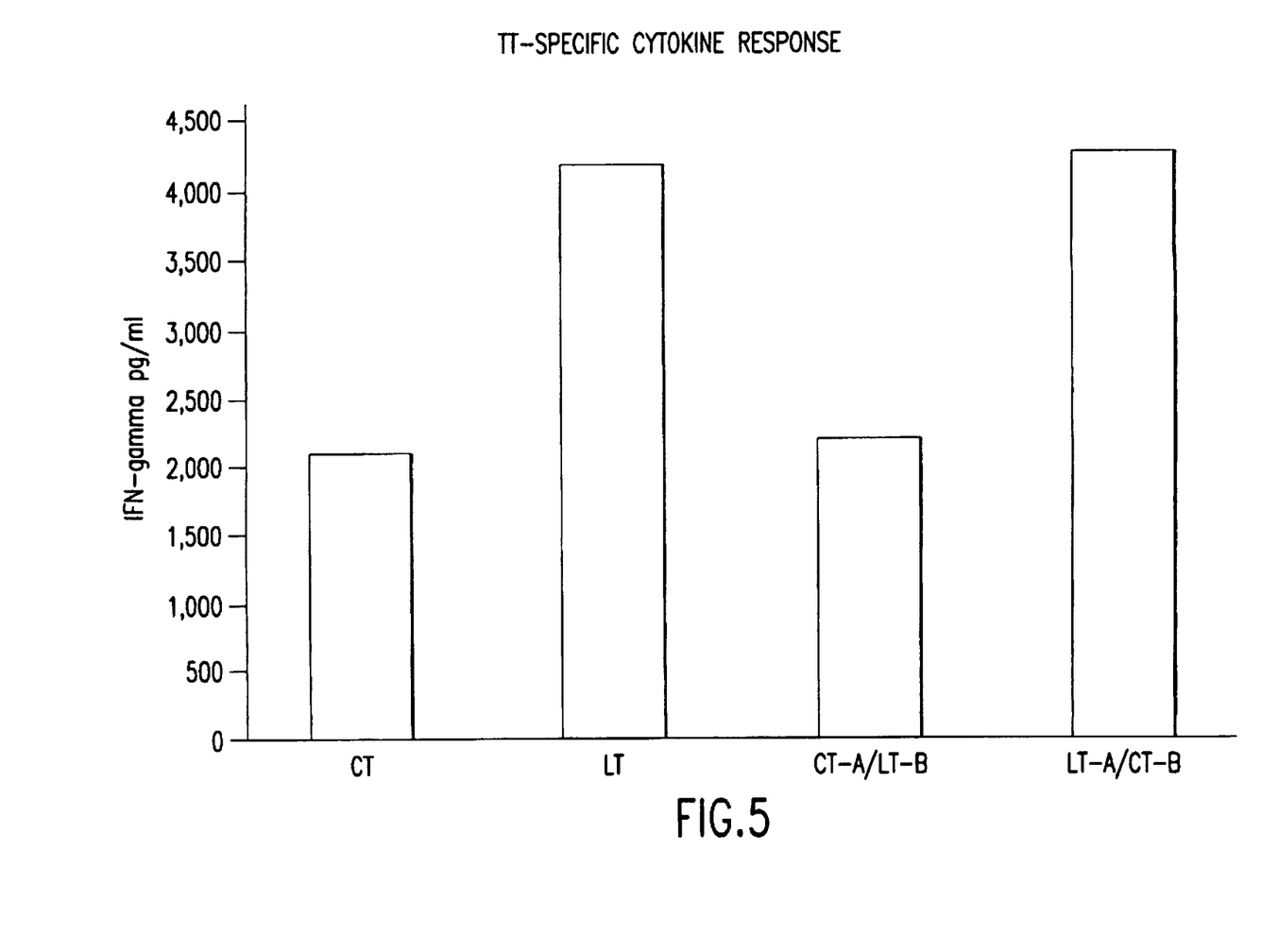

As seen in FIG. 5, LT-A/CT-B was as effective as native LT, and more effective than native CT, or CT-A/LT-B in inducing antigen-specific Th1-type cytokines; specifically, IFN-gamma, in mononuclear cells from the spleens of immunized animals, despite the significantly reduced enterotoxicity and enzymatic activity of LT-A/CT-B when compared to native LT, native CT, or CT-A/LT-B.

Figure 6:
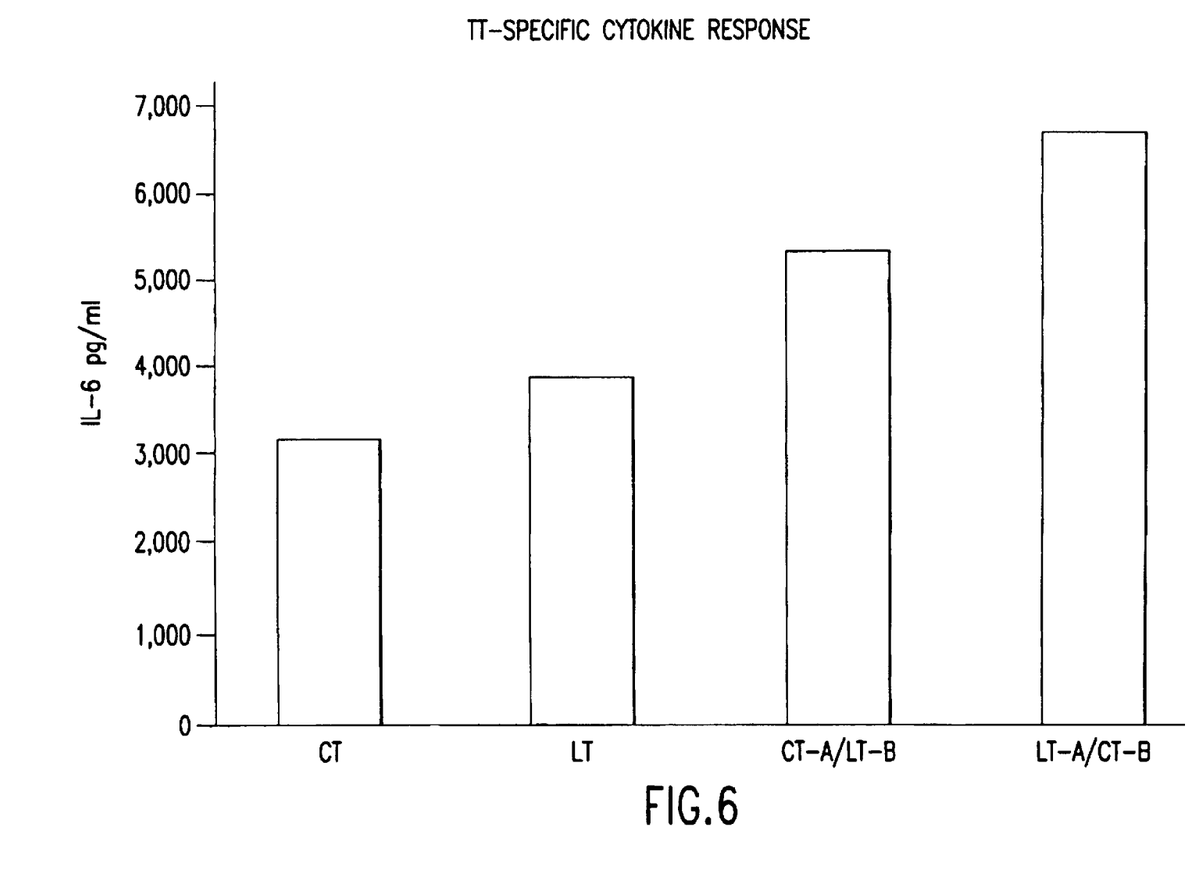

As seen in FIG. 6, LT-A/CT-B was more effective than native LT, native CT, or CT-A/LT-B in inducing antigen-specific Th2-type cytokines; specifically, IL-6, in mononuclear cells from the spleens of immunized animals, despite the significantly reduced enterotoxicity and enzymatic activity of LT-A/CT-B when compared to native LT, native CT, or CT-A/LT-B.

7. Biological Material Deposit

Plasmid pLT-A/CT-B producing LT-A/CT-B hybrid enterotoxin holotoxin has been deposited with the American Type Culture Collection (ATCC) at 10801 University Blvd., Manassas, Va. 20110–2209, USA, International Depository Authority, on Jul. 8, 2004, under the provisions of the Budapest Treaty on the International Recognition of the Deposit of Microorganisms for the Purposes of Patent Procedures, and assigned accession number PTA-6116.

Although the invention is described in detail with reference to specific embodiments thereof, it will be understood that variations which are functionally equivalent are within the scope of this invention. Indeed, various modifications of the invention in addition to those shown and described herein will become apparent to those skilled in the art from the foregoing description and accompanying drawings. Such modifications are intended to fall within the scope of the appended claims.

Various publications are cited herein, the disclosure of which are incorporated by reference in their entireties.

What is claimed is:

1. A composition comprising a LT-A/CT-B hybrid enterotoxin holotoxin recombinantly produced using plasmid pLT-A/CT-B assigned ATCC accession number PTA-6116, which holotoxin has immunologic adjuvant activity and is less toxic than native *E. coli* heat-labile enterotoxin holotoxin as measured in the patent mouse assay.

2. A composition comprising a LT-A(R192G)/CT-B hybrid enterotoxin holotoxin, which holotoxin has immunologic adjuvant activity and is less toxic than native *E. coli* heat-labile enterotoxin holotoxin as measured in the patent mouse assay.

* * * * *

SEQUENCE LISTING

<160> NUMBER OF SEQ ID NOS: 8

<210> SEQ ID NO 1
<211> LENGTH: 25
<212> TYPE: DNA
<213> ORGANISM: Artificial Sequence
<220> FEATURE:
<223> OTHER INFORMATION: Primer 1

<400> SEQUENCE: 1

-continued

```
ggctgtgggt agaattcaaa cgggg                                      25

<210> SEQ ID NO 2
<211> LENGTH: 24
<212> TYPE: DNA
<213> ORGANISM: Artificial Sequence
<220> FEATURE:
<223> OTHER INFORMATION: Primer 2

<400> SEQUENCE: 2
gaggagctcc atgtgcatat gctg                                       24

<210> SEQ ID NO 3
<211> LENGTH: 25
<212> TYPE: DNA
<213> ORGANISM: Artificial Sequence
<220> FEATURE:
<223> OTHER INFORMATION: Primer 3

<400> SEQUENCE: 3
cagcaatatg cacatggagc tcctc                                      25

<210> SEQ ID NO 4
<211> LENGTH: 24
<212> TYPE: DNA
<213> ORGANISM: Artificial Sequence
<220> FEATURE:
<223> OTHER INFORMATION: Primer 4

<400> SEQUENCE: 4
cagcatatgc acatggaaca cctc                                       24

<210> SEQ ID NO 5
<211> LENGTH: 24
<212> TYPE: DNA
<213> ORGANISM: Artificial Sequence
<220> FEATURE:
<223> OTHER INFORMATION: Primer 5

<400> SEQUENCE: 5
gaggtgttcc atgtgcatat gctg                                       24

<210> SEQ ID NO 6
<211> LENGTH: 27
<212> TYPE: DNA
<213> ORGANISM: Artificial Sequence
<220> FEATURE:
<223> OTHER INFORMATION: Primer 6

<400> SEQUENCE: 6
cctctctatg tgcatacgga acacctc                                    27

<210> SEQ ID NO 7
<211> LENGTH: 27
<212> TYPE: DNA
<213> ORGANISM: Artificial Sequence
<220> FEATURE:
<223> OTHER INFORMATION: Primer 7

<400> SEQUENCE: 7
gaggtgttcc gtatgcacat agagagc                                    27

<210> SEQ ID NO 8
<211> LENGTH: 35
<212> TYPE: DNA
```

```
<213> ORGANISM: Artificial Sequence
<220> FEATURE:
<223> OTHER INFORMATION: Primer 8

<400> SEQUENCE: 8
ccgggttgtg ggaatgctcc aggatcctcg atcag                                    35
```